US009943535B2

(12) United States Patent
Berry et al.

(10) Patent No.: US 9,943,535 B2
(45) Date of Patent: Apr. 17, 2018

(54) EDIBLE COMPOSITION COMPRISING RESVERATROL AND FLAVONOID MONOGLUCOSIDE

(71) Applicant: Conopco, Inc., Englewood Cliffs, NJ (US)

(72) Inventors: Mark John Berry, Bedfordshire (GB); Mark Ian Fowler, Bedfordshire (GB); Alan David Heath, Bangalore (IN)

(73) Assignee: CONOPCO, INC., Englewood Cliffs, NJ (US)

( * ) Notice: Subject to any disclaimer, the term of this patent is extended or adjusted under 35 U.S.C. 154(b) by 44 days.

(21) Appl. No.: 14/647,751

(22) PCT Filed: Nov. 27, 2013

(86) PCT No.: PCT/EP2013/074833
§ 371 (c)(1),
(2) Date: May 27, 2015

(87) PCT Pub. No.: WO2014/086632
PCT Pub. Date: Jun. 12, 2014

(65) Prior Publication Data
US 2015/0313927 A1    Nov. 5, 2015

(30) Foreign Application Priority Data

Dec. 6, 2012  (EP) .................................... 12195842

(51) Int. Cl.
| | | |
|---|---|---|
| A23L 1/30 | (2006.01) |
| A23L 2/52 | (2006.01) |
| A61K 31/05 | (2006.01) |
| A61K 31/7048 | (2006.01) |
| A61K 31/7034 | (2006.01) |
| A23L 33/10 | (2016.01) |
| A23L 33/105 | (2016.01) |

(52) U.S. Cl.
CPC ............ *A61K 31/7048* (2013.01); *A23L 2/52* (2013.01); *A23L 33/10* (2016.08); *A23L 33/105* (2016.08); *A61K 31/05* (2013.01); *A61K 31/7034* (2013.01); *A23V 2002/00* (2013.01); *A23V 2200/00* (2013.01)

(58) Field of Classification Search
None
See application file for complete search history.

(56) References Cited

U.S. PATENT DOCUMENTS

| 8,501,246 B2 | 8/2013 | Li |
| 2008/0152599 A1 | 6/2008 | Brignoli et al. |

FOREIGN PATENT DOCUMENTS

| CN | 101077864 | 11/2007 |
| CN | 101204358 | 6/2008 |
| WO | WO2006074278 | 7/2006 |
| WO | WO2007112996 | 10/2007 |
| WO | WO2011107494 | 9/2011 |
| WO | WO2014086632 | 6/2014 |

OTHER PUBLICATIONS

Fruit Skin and Seeds: What's Good and What's Not, http://www.seattleorganicrestaurants.com/vegan-whole-food/fruit-nutrition-seeds-skin.php, downloaded from the internet Aug. 22, 2017.*
Serving Size—The Chip Group, http://www.thechipgroup.co.nz/industrystandards2/portionsize2/, downloaded from the internet Aug. 22, 2017.*
Day et al., "Absorption of quercetin-3-glucoside and quercetin-4'-glucoside in the rat small intestine: the role of lactase phlorizin hydrolase and the sodium-dependent glucose transporter", Biochemical Pharmacology, 2003, vol. 65, No. 7, pp. 1199-1206.
Lethtoen et al., "Urinary Excretion of the Main Anthocyanin in Lingonberry (Vaccinium vitis-idaea), Cyanidin 3-O-Galactoside, and Its Metabolites", Journal of Agricultural and Food Chemistry, 2009, vol. 57, No. 10, pp. 4447-4451.
Artaria et al., Different Brands of bilberry Extract A comparison of selected components, NUTRAfoods, 2007, pp. 13-18, vol. 6 No. 4.
Baldea, Inhibition of intestinal glucose absorption by anti-diabetic medicinal plants derived from the James Bay Cree traditional pharmacopeia, Journal of Ethnopharmacology, Nov. 11, 2010, 473-482, 132, CA.
Dietmar Kammerer, Polyphenol Screening of Pomace from Red and White Grape Varieties, Journal of Agricultural and Food Chemistry, 2004, 4360-4367, 52, American Chemical Society, ., US.
Eherenkranz, Phlorizin: a review, Diabetes/Metabolism Research and Reviews, 2005, 31-38, 21, US.
Helliwell et al, The active and passive components of glucose absorption in rat jejunum under low and high perfusion stress, The Journal of Physiology, Aug. 16, 2002, 579-589, 544.3, GB.
Hongu et al, Na+-Glucose Cotransporter Inhibitors as Antidiabetic Agents II. Synthesis and Structure-Activity Relationships of 4'-Dehydroxyphlorizin Derivatives, Chemical and Pharmaceutical Bulletin, 1998, pp. 22-33; XP002169867, vol. 46 No. 1.
IPRP in PCTEP2013074833, dated Apr. 2, 2015.

(Continued)

*Primary Examiner* — Layla D Berry
(74) *Attorney, Agent, or Firm* — Foley & Lardner LLP (57) ABSTRACT

Foods or meals high in available carbohydrate such as sucrose or starch increase postprandial blood glucose concentrations. Repeated high post-prandial plasma glucose "spikes" are associated with an increased risk of developing type II diabetes. Unregulated glycemic excursions are undesirable, and any reduction or "blunting" of the post-prandial glucose concentration in blood is potentially beneficial. This invention relates to an edible composition for delay of intestinal glucose uptake through synergistic inhibition of both active sodium glucose co-transporter 1 (SGLT1) and passive glucose transporter 2 (GLUT2) leading to flattening or blunting of the post-prandial glucose peak. In a first aspect of the invention, an edible composition is provided, in the form of a single serving of one or more unit dosages, wherein the edible composition comprises 20-2000, preferably 30-1000, most preferably 40-500 mg a 3,5-dihydroxy-trans-stilbene and 10-2000, preferably 20-1000, most preferably 40-500 mg flavonoid mono-glucoside or dihydrochalcone monoglucoside.

19 Claims, 4 Drawing Sheets

(56) References Cited

OTHER PUBLICATIONS

Manzano et al, Polyphenols and phenolic acids from strawberry and apple decrease glucose uptake and transport by human intestinal Caco-2 cells, Molecular Nutrition and Food Research, May 2, 2010, 1773-1780, 54, GB.
Mintel, Antioxxidant & Greens Powder, Mintel Databse GNPD, 2011, 1-4.
Mintel, Dietary Supplement, Mintel Database GNPD, Jun. 30, 2011, 1-5.
Mintel, Mixed Berries Protein, Minel Database GNPD, 2011, 1-3.
Mintel, Resveratrol with Red Wine Supplement, Mintel Database GNPD, Apr. 30, 2008, 1-2.
Node et al., Postprandial hyperglycemia as an etiological factor in vascular failure, Cardiovascular Diabetology, 2009, pp. 1-10, 8:23.
Revilla, Analysis of several phenolic compounds with otential antioxidant properties in grap extracts and wines by high-performance liquid chromatography-photodiode array detection without sample preparation, Journal of Chromatography, 2000, 461-469, 881, ES.
Shrikhande, Win by products with health benefits, Food Research International, 2000, 469-474, 33.
Written Opinion in PCTEP2013074833, dated Oct. 28, 2014.
Wu et al, Concentrations of Anthocyanins in Common Foods in the United States and Estimation of Normal Consumption, Journal of Agricultural and Food Chemistry, Apr. 28, 2006, 4069-4075, 54, US.
X. Yue and Z. Xu, Changes of Anthocyanins, Anthocyanidins, and Antioxidant Activity in Bilberry Extract during Dry Heating, Journal of Food Science, 2008, pp. C494-C499, vol. 73 No. 6.
Aguirre et al., Electrochemical behaviour and antioxidant capacity of anthocyanins from Chilean red wine, grape and raspberry, Food Chemistry, 2010, pp. 44-48; XP55171691, vol. 121.
Svododova et al., Bilberry extract reduces UVA-induced oxidative stress in HaCaT keratinocytes: A pilot study, BioFactors, 2008, pp. 249-266; XP55171760, vol. 33.

* cited by examiner

Inhibition of Glucose Transport by Luteolin-7-Glucoside (L7G) & Resveratrol (R)

Fig. 4

Inhibition of Glucose Transport by Quercetin-3-Glucoside (Q3G) & Resveratrol (R)

Inhibition of Glucose Transport by Luteolin-7-Glucoside (L7G) & Piceatannol (P)

Fig. 8

Inhibition of Glucose Transport by Naringenin-7-Glucoside (N7G) & Piceatannol (P)

EDIBLE COMPOSITION COMPRISING RESVERATROL AND FLAVONOID MONOGLUCOSIDE

Foods or meals high in available carbohydrate such as sucrose or starch increase postprandial blood glucose concentrations. According to Node et al. (Cardiovascular diabetology, 8, 23 (2009)), repeated high post-prandial plasma glucose "spikes" are associated with an increased risk of developing type II diabetes. Unregulated glycemic excursions are undesirable, and any reduction or "blunting" of the post-prandial glucose concentration in blood is potentially beneficial. This invention relates to an edible composition for delay of intestinal glucose uptake through synergistic inhibition of both active sodium glucose co-transporter 1 (SGLT1) and passive glucose transporter 2 (GLUT2) leading to flattening or blunting of the post-prandial glucose peak.

Annushka Klitkovena Supplement is a product described to help different ailments including muscle and bone pain, cellulite, diabetes, prostate and veins, and protect against radioactive effects and to clean the body. The supplement is made with wheat sprouts and grape seeds. According to Kammerer et al (J. Agric. Food Chem., 52 (14), 4360-4367 (2004)), grape seeds contain 0.0014 w/w resveratrol. Wheat sprouts also appear to be absent of resveratrol.

SUMMARY OF THE INVENTION

In a first aspect of the invention, an edible composition is provided, in the form of a single serving of one or more unit dosages, wherein the edible composition comprises 20-2000, preferably 30-1000, most preferably 40-500 mg a 3,5-dihydroxy-trans-stilbene and 10-2000, preferably 20-1000, most preferably 40-500 mg flavonoid monoglucoside or dihydrochalcone monoglucoside.

In a second aspect of the invention, a method of reducing post-prandial blood glucose peak amplitude or glycemic response in a diabetic or non-diabetic person is provided, the method comprising the steps of:
(a) oral administration of the compositions of any one of the preceding claims to the diabetic or non-diabetic person; and
(b) oral administration of saccharide to the diabetic or non-diabetic person;
wherein step (a) is simultaneous with, precedes by 0 to 90, preferably 0 to 60 minutes, or follows by 0 to 30 minutes step (b), and
wherein the saccharide comprises or is glucose.

In a third aspect of the invention, a method for treating a person in need thereof for type 2 diabetes is provided, the method comprising the steps of:
(a) oral administration of the compositions of any one of claims 1 to 9 to the person in need thereof; and
(b) oral administration of saccharide to the person in need thereof;
wherein step (a) is simultaneous with, precedes by 0 to 90, preferably 0 to 60 minutes, or follows by 0 to 30 minutes step (b), and
wherein the saccharide comprises or is glucose.

BRIEF DESCRIPTION OF THE FIGURES

The invention is illustrated with reference to the figures which show in.

DETAILED DESCRIPTION OF THE INVENTION

In a first aspect of the invention, an edible composition is provided, in the form of a single serving of one or more unit dosages, wherein the edible composition comprises 20-2000, preferably 30-1000, most preferably 40-500 mg a 3,5-dihydroxy-trans-stilbene and 10-2000, preferably 20-1000, most preferably 40-500 mg flavonoid monoglucoside or dihydrochalcone monoglucoside.

The 3,5-dihydroxy-trans-stilbene can be selected from the group consisting of resveratrol, piceatannol and mixtures thereof.

The flavonoid monoglucoside is an SGLT1 inhibitor.

The flavonoid monoglucoside may be selected from the group consisting of a flavone monoglucoside, flavonol monoglucoside, a flavanol monoglucoside, a flavanone monoglucoside, an isoflavone monoglucoside, a flavan monoglucoside, an isoflavan monoglucoside, a flavan-3-ol monoglucoside, an anthocyanidin monoglucoside, a chalcone monoglucoside, a flavanolignan monoglucoside and mixtures thereof. Preferably, the flavonoid monoglucoside is selected from the group consisting of a flavone monoglucoside, flavonol monoglucoside and mixtures thereof.

In particular, the flavonoid monoglucoside may be selected from the group consisting of luteolin-7-glucoside, apigenin-7-glucoside, apigenin-8-C-glucoside, kaempferol-7-O-glucoside, kaempferol-3-O-glucoside, quercetin-3-glucoside, quercetin-4-glucoside, naringenin-7-O-glucoside, eriodictyol-7-O-glucoside, daidzein-8-C-glucoside, daidzein-7-glucoside, cyanidin-3-glucoside, malvidin-3-O-glucoside, delphinidin-3-glucoside, pelargonidin-3-glucoside and mixtures thereof. Preferably the flavonoid monoglucoside is selected from the group consisting of luteolin-7-glucoside, quercetin-3-glucoside and mixtures thereof.

The dihydrochalcone monoglucoside is preferably phloridzin.

In one embodiment, the flavonoid monoglucoside or dihydrochalcone monoglucoside is at least 20%, preferably at least 40%, most preferably at least 60% more resistant to hydrolysis by lactase phloridzin hydrolase than quercetin-4-glucoside.

Lactase phloridzin hydrolyase (LPH), a beta-galactosidase, is an enzyme found in the small intestine involved in the hydrolysis of the disaccharide lactose into its constituent galactose and glucose monomers. In particular, the enzyme hydrolyses the beta-glycosidic bond in D-lactose. Deficiency of this enzyme causes lactose intolerance. LPH also has glucosidase activity. Thus it is essential that the flavonoid glucoside or dihydrochalcone monoglucoside exhibits a degree of resistance to hydrolysis by LPH in the small intestine where glucose absorption, via the glucose transporters, takes place.

By the term "at least 20% more resistant to hydrolysis by LPH than quercetin-4-glucoside" is meant that the rate of hydrolysis by LPH is at least 20% lower than that for quercetin-4'-glucoside. Thus the rate would be zero if 100% more resistant to hydrolysis by LPH than quercetin-4-glucoside.

Thus the flavonoid monoglucoside is preferably selected from the group consisting of luteolin-7-glucoside, apigenin-8-C-glucoside, kaempferol-7-O-glucoside, kaempferol-3-O-glucoside, quercetin-3-glucoside, naringenin-7-O-glucoside, daidzein-8-C-glucoside, pelargonidin-3-glucoside and mixtures thereof, as all the foregoing flavonoid monoglucosides have been shown to be at least 20% more resistant to hydrolysis by LPH than quercetin-4-glucoside.

Thus the dihydrochalcone monoglucoside is preferably phloridzin, as it has been shown to be at least 20% more resistant to hydrolysis by LPH than quercetin-4-glucoside.

Preferably the molar ratio of resveratrol to flavonoid monoglucoside or dihydrochalcone monoglucoside is in the range 20:1 to 1:20, preferably 10:1 to 1:10, most preferably 1:1 to 1:10.

The composition of the first aspect of the invention may be a foodstuff selected from the group consisting of a beverage, a supplement, a soup, margarine, a ready-to-eat meal, a dressing, a mayonnaise, mustard, a tomato-based condiment, a sauce, a seasoning, yoghurt and a frozen confection.

In general terms, the composition may be in the form of a solid, a slurry, a solution, a suspension, a gel or an emulsion.

More specifically, the composition may be in the form of a beverage, in particular a fruit or tea based beverage.

The composition may be in the form of a supplement of one or more unit dosages such as capsules, cachets, lozenges, pills, tablets, caplets, each comprising a predetermined amount of resveratrol and flavonoid monoglucoside.

The composition may be a soup in dry, paste or liquid form.

The composition may be a seasoning sold as unit doses in the form of a powder, a compressed powder in the form of, for example, a cube, a liquid or suspension, or a gel.

The term "frozen confection" means a sweet-tasting fabricated foodstuff intended for consumption in the frozen state (i.e. under conditions wherein the temperature of the foodstuff is less than 0° C., and preferably under conditions wherein the foodstuff comprises significant amounts of ice). Frozen confections include ice cream, sorbet, sherbet, frozen yoghurt, water ice, milk ice and the like. Preferably the frozen confection has a total solids content (i.e. the sum of the weights of all the ingredients other than water, expressed as a percentage of the total weight) of at least 20%, more preferably at least 25%. Frozen confections may be aerated or unaerated. Preferably the frozen confection is aerated. The frozen confection may be manufactured by any suitable process, typically by preparing a mix of ingredients; then pasteurising and optionally homogenising the mix; and then freezing and optionally aerating the mix to produce the frozen confection.

In a second aspect of the invention, a method of reducing post-prandial blood glucose peak amplitude or glycemic response in a diabetic or non-diabetic person is provided, the method comprising the steps of:
(a) oral administration of the compositions of the first aspect of the invention to the diabetic or non-diabetic person; and
(b) oral administration of saccharide to the diabetic or non-diabetic person;
wherein step (a) is simultaneous with, precedes by 0 to 90, preferably 0 to 60 minutes, or follows by 0 to 30 minutes step (b), and
wherein the saccharide comprises or is glucose.

In a third aspect of the invention, a method for treating a person in need thereof for type 2 diabetes is provided, the method comprising the steps of:
(a) oral administration of the compositions of the first aspect of the invention to the person in need thereof; and
(b) oral administration of saccharide to the person in need thereof;
wherein step (a) is simultaneous with, precedes by 0 to 90, preferably 0 to 60 minutes, or follows by 0 to 30 minutes step (b), and
wherein the saccharide comprises or is glucose.

In the second and third aspects of the invention, the saccharide may be selected from the group consisting of polysaccharide, oligosaccharide, disaccharide, monosaccharide and mixtures thereof.

In the alternative, use of the composition of the first aspect of the invention is provided for reducing post-prandial blood glucose peak amplitude or glycemic response in a diabetic or non-diabetic person.

In the alternative, the composition of the first aspect of the invention is provided for use in the treatment of type 2 diabetes.

In a further alternative, use of the composition of the first aspect of the invention is provided for the manufacture of a medicament for treatment of type 2 diabetes.

EXAMPLE 1

Identification of SGLT1 and GLUT2 Inhibitors

Routine Cell Culture

Human epithelial colorectal adenocarcinoma (Caco-2) cells were obtained from the American Type Culture Collection (ATCC) and cultured in Growth Medium consisting of Dulbecco's modified Eagle's medium (containing Glutamax-1, 4.5 g/L D-glucose and 25 mM 4-(2-hydroxyethyl)-1-piperazine ethanesulphonic acid (Hepes) (Invitrogen)), 10% foetal bovine serum (Sigma), 1% non-essential amino acids (Invitrogen) and 1 mM sodium pyruvate (Sigma)). The cells were routinely passaged at approximately 80% confluence using TrypLE™ Express Stable Trypsin-Like Enzyme (Invitrogen) to detach the cells, and seeded at approximately 114 cells per mm$^2$ in fresh tissue culture flasks. Only cells between the passage numbers 45 and 49 were used for experiments.

Preparation of Differentiated Caco-2 Cell Monolayers

Corning® HTS Transwell® 96 well permeable insert supports (Sigma) were collagen coated with 40 µl of 50 µg/ml rat tail collagen type I (BD Biosciences) in 0.02 M acetic acid for one hour at room temperature under sterile conditions. The inserts were washed twice in phosphate buffered saline (PBS (Invitrogen)) and the Caco-2 cells seeded into the inserts at 9.6×10$^5$ cell/ml (75 µl per insert) in Growth Medium and 30 ml of Growth Medium added to the feeder plate below. The cells were left to attach to the collagen matrix and form monolayers over 48 hours at 37° C., 5% $CO_2$. Both inserts and feeder plate were washed in PBS and the cells incubated with BD Entero-STIM™ Enterocyte Differentiation Medium containing MITO+™ Serum Extender solution (both BD Biosciences), 75 µl per insert and 30 ml in the feeder plate, for a further 48 hours at 37° C., 5% $CO_2$.

Glucose Transport Inhibitor Cell Screening Assay

Differentiated cell monolayers were washed gently in Dulbecco's Phosphate Buffered Saline containing $CaCl_2$ and $MgCl_2$ (PBS(+) (Invitrogen)) and the inserts transferred to a new Corning® HTS Transwell®-96 well receiver plate (Sigma). The cells were incubated with fresh PBS(+) (75 µl per insert and 225 µl per well) for 60 minutes at 37° C., 5% $CO_2$. The PBS(+) was gently aspirated and replaced with 75 µl per insert of either 5 mM D-glucose (Sigma)±test active or 25 mM D-glucose±test active in triplicate and 225 µl per well of PBS(+) quickly added to each well. The 5 mM glucose wells and the 25 mM glucose wells were incubated at 37° C., 5% $CO_2$ for 15 minutes and 30 minutes, respectively. Details of all the actives tested are found in table 1. The cell inserts were transferred to a new receiver plate, the supernatant gently aspirated from the cells and replaced with 100 µl of 100 µM of Lucifer Yellow (Sigma) solution to confirm the integrity of the monolayers. 225 µl of PBS(+) was added to each well and incubated at 37° C., 5% $CO_2$ for 1 hour. The cell inserts were then discarded and the permeability of the membranes to Lucifer Yellow checked by measuring the fluorescence of the samples at 485 nm (excitation) and 530 nm (emission) on a Spectramax Gemini EM fluorescence microplate reader.

Glucose Assay

The amount of glucose transported across the cell monolayers was measured using a glucose assay based on Invitrogen's Amplex Red Glucose/Glucose oxidase Assay Kit. Briefly, 50 µl of each test sample was transferred to a black sided/clear bottom 96-well plate (Greiner Bio-One) to which 100 µl of reaction buffer (0.5 µl 10 mM Ampliflu Red, 1 µl 10U/ml Horse Radish peroxidase, 1 µl 100U/ml glucose oxidase and 97.5 µl PBS (all Sigma)) was added. After 10 minutes incubation at room temperature, the fluorescence of the samples were measured at 530 nm (excitation) and 590 nm (emission) on a Spectramax Gemini EM fluorescence microplate reader and the glucose concentration extrapolated from a standard curve.

Results

Table 1 shows the percentage of inhibition of each test active against the transport of glucose across a differentiated Caco-2 cell monolayer. At the lower D-glucose concentration of 5 mM, the early transport of glucose across the cell monolayer is predominantly through the apically expressed, high affinity, low capacity SGLT1 glucose transporter. At higher D-glucose concentrations, the SGLT1 transporter becomes saturated and consequently the majority of glucose transport across the monolayer is driven by the low affinity, high capacity GLUT2 transporter that is targeted to the apical membrane only following an initial SGLT1-dependent transport of glucose. The screening cell model, detailed in the methods above, is designed to take advantage of these differences in the optimal conditions for each transporter to identify both SGLT1 and GLUT2 specific inhibitors. While both SGLT1 and GLUT2 on the apical membrane transport glucose into the enterocyte, GLUT2 is also expressed in the basolateral membrane where it is essential for the transport of glucose out of the cell. Hence, GLUT2 specific inhibitors will not only block the apically targeted transporters at high D-glucose concentrations (25 mM), they will also enter the cell and block the exit of glucose from the enterocyte at low D-glucose concentrations (5 mM). Therefore, to differentiate between inhibition of apical and basolateral transporters, each active was tested at both 5 mM D-glucose for 15 minutes and 25 mM D-glucose for 30 minutes. Actives were classed as SGLT1 inhibitors if they exhibited at least 20% inhibition of glucose transport at 5 mM D-glucose and a corresponding no more than 20% inhibition at 25 mM D-glucose. Actives that were able to inhibit glucose transport by at least 20% in both conditions were classed as GLUT2 specific inhibitors. This approach was qualified through the use of the widely recognised specific inhibitors of both SGLT1 and GLUT2, namely phloridzin and phloretin respectively.

Figure 1:
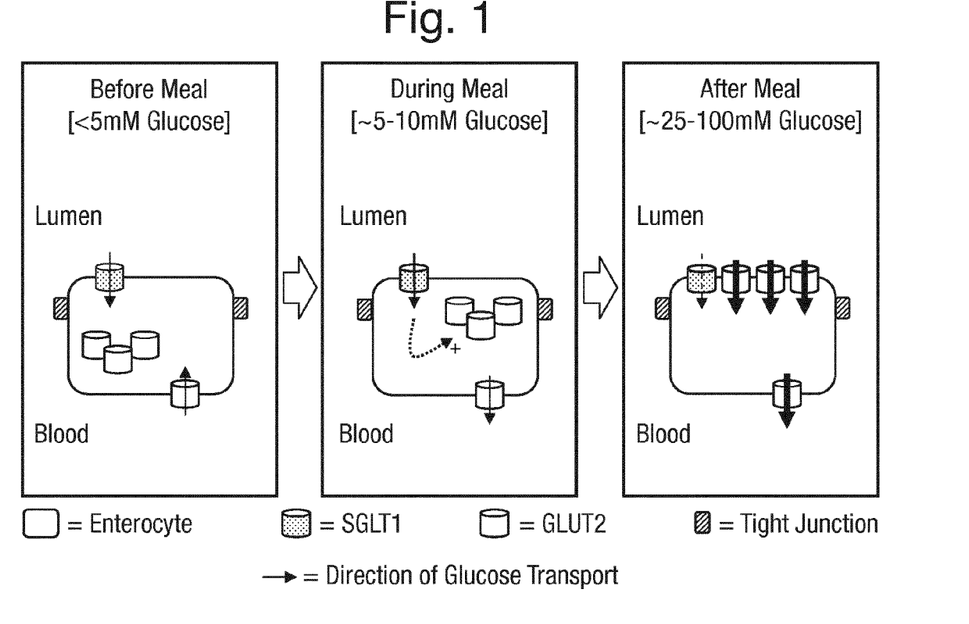
FIG. 1 a model of the glucose concentration timeline during a meal.

The foregoing glucose transport cell model was described by Kellett et al. (Diabetes, 54, 10, 3056-62 (2005)) and illustrated by FIG. 1 designed to mimic the localised changes in glucose concentration in the small intestine during the consumption of a carbohydrate rich meal. Before the meal, the concentration of free glucose in the lumen of the intestine is low (<5 mM) and the apically expressed SGLT1 transporter actively transports any available glucose into the enterocyte. GLUT2 transporters are also active on the basolateral membrane of the enterocyte, transporting glucose from the blood into the cell to maintain cellular metabolism if required. During a meal, the local concentration of glucose begins to increase (5-10 mM) and is transported from the intestinal lumen by SGLT1 and subsequently into the systemic circulation via GLUT2. As a consequence of this initial glucose transport across the enterocyte, intracellular stores of GLUT2 are mobilised and targeted to the apical membrane. Shortly after the meal, very high local concentrations of glucose occur (25-100 mM) as the carbohydrate content of the meal is broken down into monosaccharides by alpha-glucosidase enzymes located on the apical enterocyte membrane. At these high levels of glucose, the high affinity, low capacity transporter SGLT1 becomes saturated and the majority of glucose transport across the enterocyte is due to the low affinity, high capacity GLUT2 transporters now present in the apical membrane.

Table 1 demonstrates that for inhibition of SGLT1, a flavonoid monoglucoside or dihydrochalcone monoglucoside is required as confirmed by phloridzin, luteolin-7-glucoside, apigenin-7-glucoside, apigenin-8-c-glucoside, kaempferol-3-glucoside, kaempferol-7-glucoside, quercetin-3-glucoside, quercetin-4-glucoside, naringenin-7-glucoside, eriodictiol-7-glucoside, daidzein-8-c-glucoside, daidzein-7-glucoside, cyanidin-3-glucoside, malvidin-3-o-glucoside, delphinidin-3-glucoside and pelargonidin-3-glucoside. Indeed, the presence of an additional glucose moiety on the chemical structure destroys this inhibitory action as demonstrated by quercetin-3,4'-diglucoside. The specificity for a glucoside is confirmed by the absence of SGLT1 inhibitory activity by other flavonoid glycosides tested, including cyanidin-3-rutinoside and malvidin-3-O-galactoside. In addition, the lack of SGLT1 inhibitory activity shown by the hydroquinone monoglucoside, arbutin, reinforces the importance of a flavonoid and dihydrochalcone structures in the glucoside molecule. Other non-flavonoid glucosides (except dihydrochalcone monoglucosides) alleged by Welsch et al. (J. of Nutrition, 119, 11, 1698-704 (1989)) to be glucose transporter inibitors such as chlorogenic acid, caffeic acid and rosmarinic acid (an ester of caffeic acid) showed no inhibitory activity in this cell model for either SGLT1 or GLUT2 inhibition. Table 1 also shows that the non-methylated stilbenes resveratrol and piceatannol are GLUT2 inhibitors and pterostilbene (a methylated stilbene) is neither an SGLT1 nor a GLUT2 inhibitor.

EXAMPLE 2

Synergy Between SGLT1 and Resveratrol

Preparation of Differentiated Caco-2 Cell Monolayers

Caco-2 cells were cultured and routinely passaged as described in example 1. Caco-2 cells were seeded into BioCoat HTS Fibrillar Collagen Multiwell Inserts (BD Biosciences) at $2.5 \times 10^5$ cell/ml (500 µl per insert) in Growth Medium and 30 ml of Growth Medium added to the feeder plate below. The cells were left to attach to the collagen matrix and form monolayers over 24 hours at 37° C., 5% $CO_2$. Both inserts and feeder plate were washed in PBS and the cells incubated with BD Entero-STIM™ Enterocyte Differentiation Medium containing MITO+™ Serum Extender solution (both BD Biosciences), 500 µl per insert and 30 ml in feeder plate, for a further 48 hours at 37° C., 5% $CO_2$.

TABLE 1

Actives tested for SGLT1 and GLUT2 inhibition activity in Caco-2 cells using 5 mM D-glucose for 15 minutes and 25 mM D-glucose for 30 minutes, respectively.

| Chemical Family: | | Test Active[a] | Solvent | % Glucose Transport inhibition 5 mM | 25 mM | Class[b] | Supplier |
|---|---|---|---|---|---|---|---|
| Flavonoids | Dihydrochalcone | Phloridzin | EtOH | 57.57 | 18.42 | SGLT1 | Sigma |
| | Flavones | Luteolin-7-glucoside | DMSO | 44.09 | 17.03 | SGLT1 | Extrasynthese |
| | | Apigenin-7-glucoside | DMSO | 37.97 | 12.81 | SGLT1 | Extrasynthese |
| | | Apigenin-8-C-glucoside | DMSO | 33.84 | 5.76 | SGLT1 | Extrasynthese |
| | Flavonols | Kaempferol 7-O-glucoside | DMSO | 43.89 | 14.42 | SGLT1 | Extrasynthese |
| | | Kaempferol 3-O-glucoside | DMSO | 53.89 | 19.12 | SGLT1 | Extrasynthese |
| | | Quercetin-3-glucoside | DMSO | 46.40 | 12.20 | SGLT1 | PlantChem |
| | | Quercetin-4-glucoside | DMSO | 43.20 | 19.05 | SGLT1 | PlantChem |
| | | Quercetin-3,4'-diglucoside | DMSO | 17.48 | Nt | None | PlantChem |
| | Flavanones | Naringenin-7-O-glucoside | DMSO | 29.56 | 0.06 | SGLT1 | Extrasynthese |
| | | Eriodictyol-7-O-glucoside | DMSO | 38.88 | 4.98 | SGLT1 | Extrasynthese |
| | Isoflavones | Daidzein-8-C-glucoside | DMSO | 20.31 | 12.88 | SGLT1 | Sigma |
| | | Daidzein-7-glucoside | DMSO | 35.03 | 7.23 | SGLT1 | Extrasynthese |
| | Anthocyanidins | Cyanidin | DMSO | 7.93 | 3.21 | None | ChromaDex |
| | | Pelargonidin | DMSO | 4.07 | 16.48 | None | ChromaDex |
| | | Malvidin | DMSO | 14.21 | 4.99 | None | ChromaDex |
| | | Delphinindin | DMSO | 0.01 | 15.86 | None | ChromaDex |
| | | Cyanidin-3-glucoside | DMSO | 42.48 | ND | SGLT1 | Extrasynthese |
| | | Cyanidin-3-rutinoside | DMSO | 19.42 | ND | None | Extrasynthese |
| | | Malvidin-3-O-glucoside | DMSO | 22.92 | 10.91 | SGLT1 | Extrasynthese |
| | | Delphinidin-3-glucoside | DMSO | 41.27 | 13.58 | SGLT1 | Extrasynthese |
| | | Pelargonidin-3-glucoside | DMSO | 27.30 | ND | SGLT1 | Extrasynthese |
| | | Malvidin 3-O-Galactoside | DMSO | 19.05 | 10.41 | None | Sigma |
| Non-methylated Stilbene | | Resveratrol | DMSO | 76.07 | 59.05 | GLUT2 | DSM Nutritional Products |
| | | Piceatannol | DMSO | 89.28 | 32.73 | GLUT2 | Sigma |
| Methylated Stilbene | | Pterostilbene | DMSO | 18.44 | 8.26 | None | Sigma |

[a]All actives tested at 150 uM and 300 uM for GLUT2 inhibition and SGLT1 inhibition assays respectively.
[b]Based on SGLT1 inhibitors having >20% inhibition at 5 mM (glucose) and <20% inhibition at 25 mM, and GLUT2 having >20% inhibition at both 5 mM & 25 mM
ND—Not detected,
Nt—Not tested
The assigned class of transporter inhibited by each active is based on SGLT1 inhibitors having ≥20% inhibition of glucose transport at 5 mM D-glucose and ≤20% inhibition at 25 mM D-glucose, and GLUT2 inhibitors having ≥20% inhibition at both 5 mM and 25 mM D-glucose levels. ND = not detected; Nt = not tested.

Glucose Transport Cell Model

Differentiated cell monolayers were washed gently in PBS(+) and the inserts transferred to a new standard tissue culture 24-well plate. The cells were incubated with fresh PBS(+) (500 µl per insert and 1 ml per well) for 30 minutes at 37° C. 5% $CO_2$. The PBS(+) was gently aspirated and replaced with 250 µl per insert of 5 mM D-glucose±test active and 1 ml of PBS(+) quickly added to each well below before the cells were replaced in the incubator at 37° C. 5% $CO_2$. After 15 minutes, the cell inserts were transferred to a new 24-well plate, and a further 250 µl of 45 mM D-glucose±test active was added to each insert (resulting in a final concentration of glucose of 25 mM) and again 1 ml of PBS(+) added to the wells. After a further 15 minutes the inserts were again transferred to a new 24-well plate and this time only fresh PBS(+) was added to the wells below. This step was repeated after another 15 minutes. The cell inserts were transferred to a new 24-well plate, the supernatant gently aspirated from the cells and replaced with 500 µl of 100 µM of Lucifer Yellow (Sigma) solution to confirm the integrity of the monolayers. 1 ml of PBS(+) was added to each well and incubated at 37° C., 5% $CO_2$ for 1 hour. The cell inserts were then discarded and the permeability of the membranes to Lucifer Yellow was checked by measuring the fluorescence of the samples at 485 nm (excitation) and 530 nm (emission) on a Spectramax Gemini EM fluorescence microplate reader.

Glucose Assay

After the last incubation, all of the retained PBS(+) from each step (i.e. at 15, 30, 45 and 60 minutes) was assayed for glucose levels as described in example 1, and the total cumulative glucose transport calculated. The localised changes in luminal glucose concentrations described and illustrated in example 1 are mimicked in-vitro through an initial short incubation of differentiated Caco-2 cells with a low level of D-glucose (5 mM for 15 minutes) immediately followed by a sustained incubation with a high level of D-glucose (final concentration of 25 mM for 45 minutes).

Results

Figure 2:
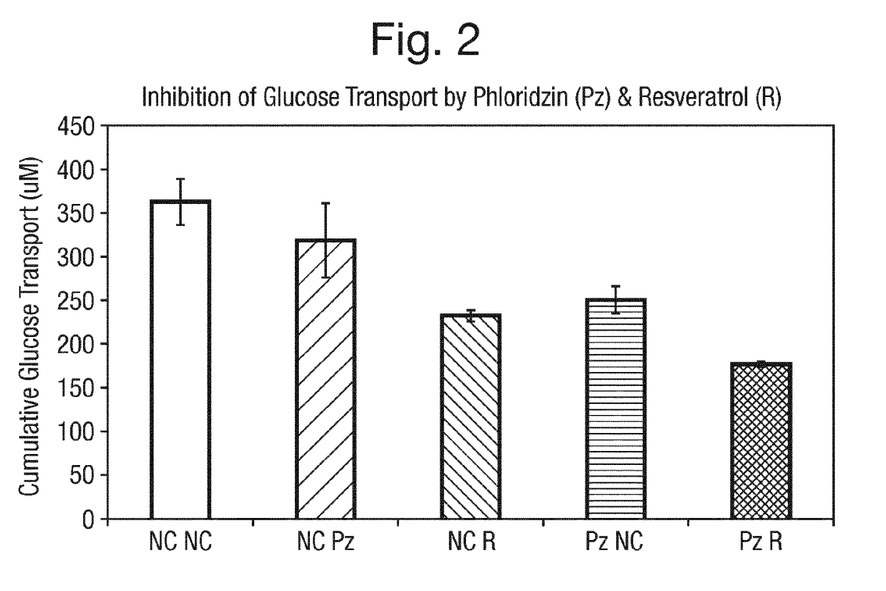
FIG. 2 the total cumulative glucose transport ($\mu$M) across differentiated Caco-2 monolayers in the presence or absence of a SGLT1 inhibitor (300 $\mu$M phloridzin (Pz)) for the first 15 minutes in 5 mM D-glucose and subsequently in the presence or absence of 75 $\mu$M resveratrol (R) in 25 mM D-glucose for the remaining 45 minutes (NC=vehicle negative control)
Figure 3:
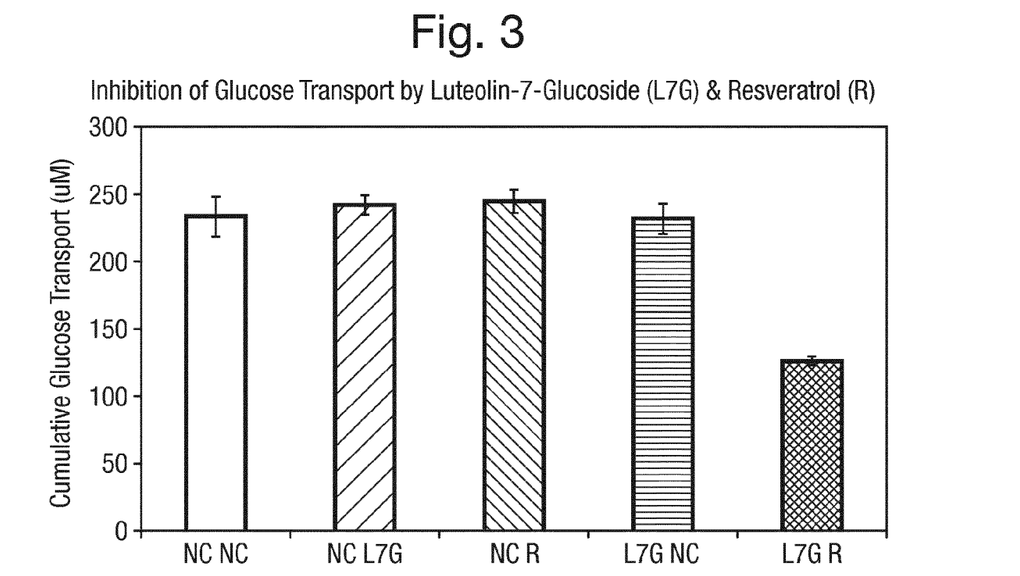
FIG. 3 the total cumulative glucose transport ($\mu$M) across differentiated Caco-2 monolayers in the presence or absence of a SGLT1 inhibitor (300 $\mu$M luteolin-7-glucoside (L7G)) for the first 15 minutes in 5 mM D-glucose and subsequently in the presence or absence of 50 $\mu$M resveratrol (R) in 25 mM D-glucose for the remaining 45 minutes (NC=vehicle negative control)
Figure 4:
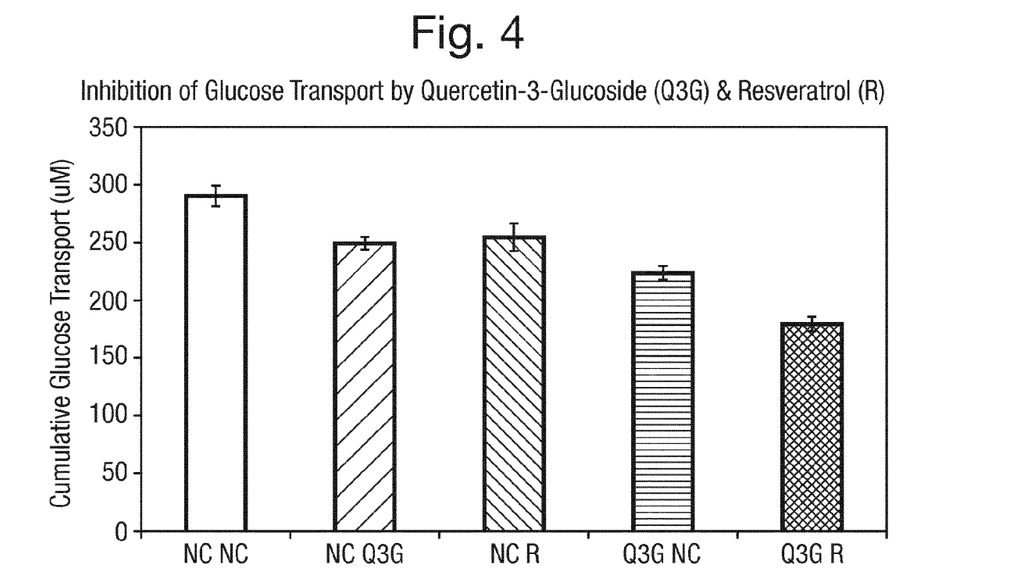
FIG. 4 the total cumulative glucose transport ($\mu$M) across differentiated Caco-2 monolayers in the presence or absence of a SGLT1 inhibitor (300 $\mu$M quercetin-3-glucoside (Q3G)) for the first 15 minutes in 5 mM D-glucose and subsequently in the presence or absence of 75 $\mu$M resveratrol (R) in 25 mM D-glucose for the remaining 45 minutes (NC=vehicle negative control)
Figure 5:
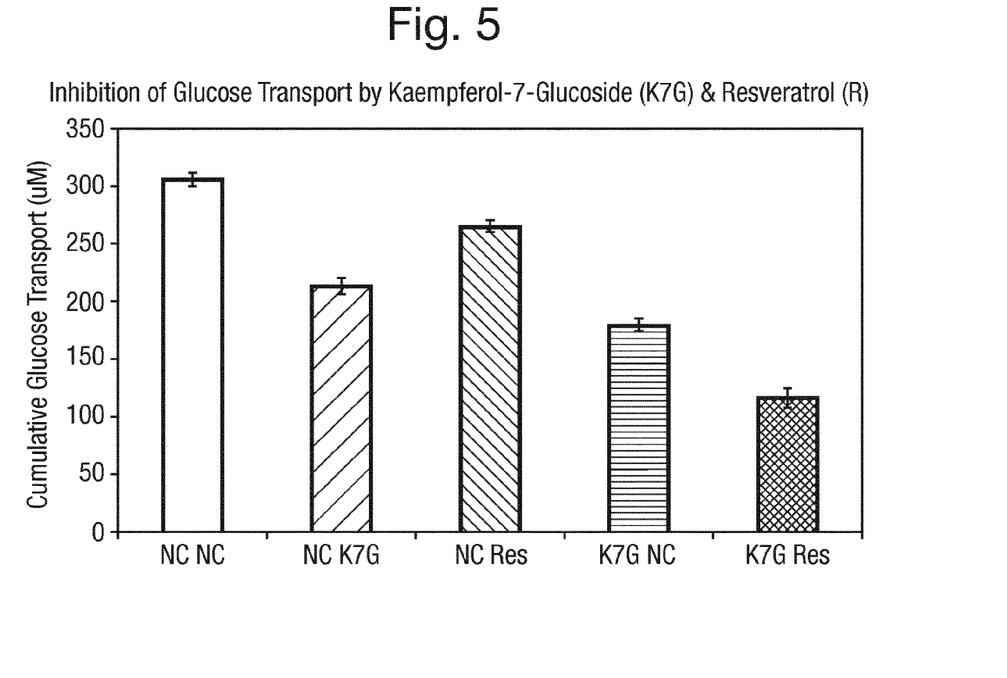
FIG. 5 the total cumulative glucose transport ($\mu$M) across differentiated Caco-2 monolayers in the presence or absence of a SGLT1 inhibitor (300 $\mu$M Kaempferol-7-glucoside (K7G)) for the first 15 minutes in 5 mM D-glucose and subsequently in the presence or absence of a GLUT2 inhibitor (75 $\mu$M Resveratrol (R)) in 25 mM D-glucose for the remaining 45 minutes (NC=vehicle negative control)
Figure 6:
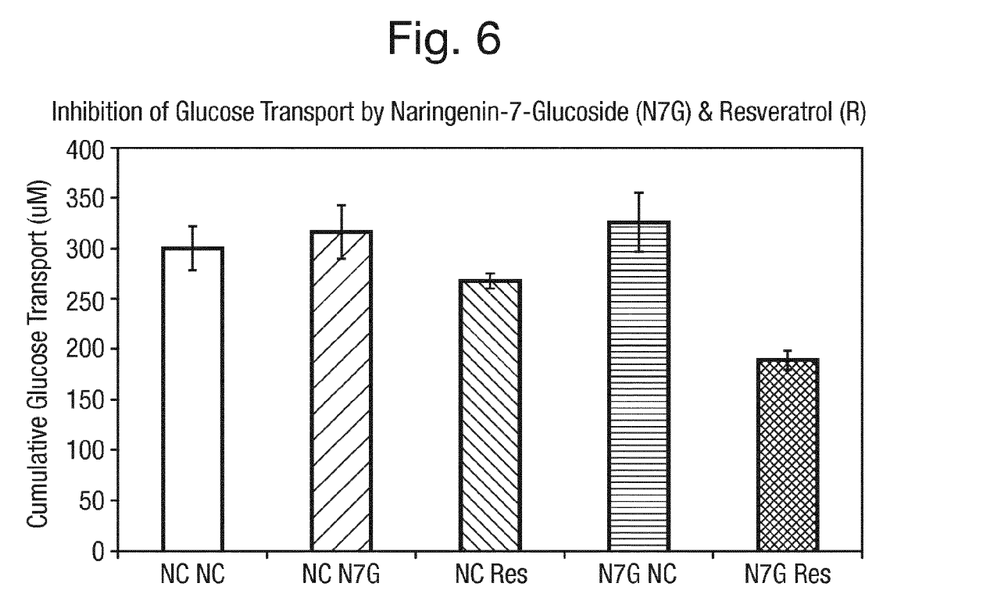
FIG. 6 the total cumulative glucose transport (pM) across differentiated Caco-2 monolayers in the presence or absence of a SGLT1 inhibitor (300 $\mu$M Naringenin-7-glucoside (N7G)) for the first 15 minutes in 5 mM D-glucose and subsequently in the presence or absence of a GLUT2 inhibitor (75 $\mu$M Resveratrol (R)) in 25 mM D-glucose for the remaining 45 minutes (NC=vehicle negative control)
Figure 7:
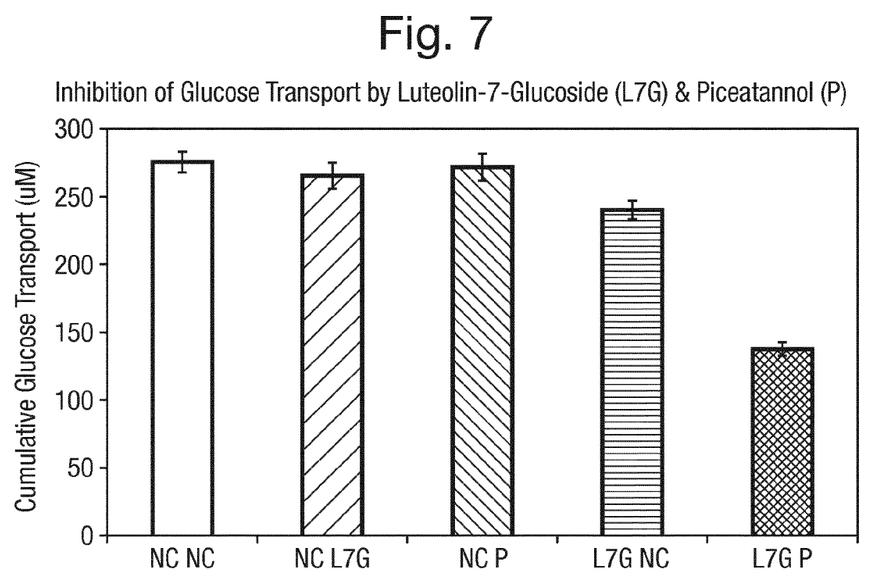
FIG. 7 the total cumulative glucose transport ($\mu$M) across differentiated Caco-2 monolayers in the presence or absence of a SGLT1 inhibitor (300 $\mu$M Luteolin-7-glucoside(L7G)) for the first 15 minutes in 5 mM D-glucose and subsequently in the presence or absence of a GLUT2 inhibitor (75 $\mu$M Piceatannol (P)) in 25 mM D-glucose for the remaining 45 minutes (NC=vehicle negative control)
Figure 8:
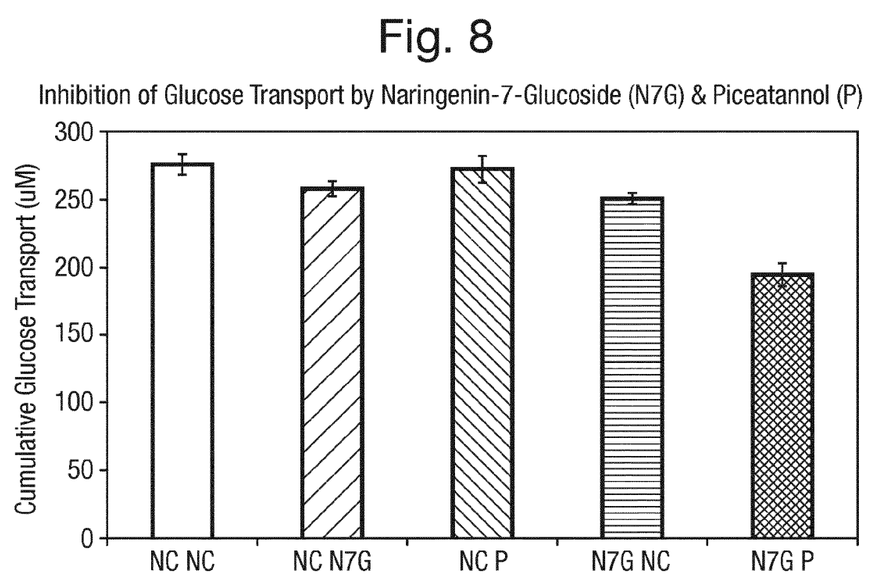
FIG. 8 the total cumulative glucose transport ($\mu$M) across differentiated Caco-2 monolayers in the presence or absence of a SGLT1 inhibitor (300 $\mu$M Naringenin-7-glucoside (N7G)) for the first 15 minutes in 5 mM D-glucose and subsequently in the presence or absence of a GLUT2 inhibitor (75 $\mu$M Piceatannol (P)) in 25 mM D-glucose for the remaining 45 minutes (NC=vehicle negative control).

FIG. 2 plots the total cumulative glucose transport across differentiated Caco-2 monolayers in the presence or absence of the SGLT1 inhibitor phloridzin (Pz) for the first 15 minutes in 5 mM D-glucose and subsequently in the presence or absence of the GLUT2 inhibitor resveratrol (R) in 25 mM D-glucose for the remaining 45 minutes. The SGLT1 specific inhibitor, phloridzin (Pz), shows a significant reduction in total Cumulative Glucose Transport (tCGT) when added from the beginning of the cell system (Pz NC), demonstrating the inhibition of SGLT1 which is the dominant active transporter at low glucose levels. However Pz exhibits no inhibition on tCGT when added later with the high concentration of D-glucose (NC Pz) since the SGLT1 transporters are now saturated and glucose transport is now dependent on the high capacity GLUT2 transporters. The GLUT2 specific inhibitor, resveratrol (R), demonstrates a significant reduction in tCGT when added with the high concentration of D-glucose as expected (NC R). However a combination of 300 µM Pz at low glucose concentrations, followed by 75 µM R at the high glucose concentration appears to significantly and synergistically inhibit the tCGT. This synergy exploits the requirement of an initial transport of glucose into the enterocyte by SGLT1 before the high-capacity GLUT2 can be targeted to the apical membrane. Used in combination, both SGLT1 and GLUT inhibitors can synergistically inhibit the localised uptake of glucose from the intestinal lumen and hence reduce the high 'spikes' of postprandial blood glucose associated with the onset of type 2 diabetes.

Further examples are shown in FIGS. 3 to 8 which show respectively the synergies between 300 µM of the SGLT1 inhibitor luteolin-7-glucoside (L7G)) and 50 µM resveratrol (R), 300 µM of the SGLT1 inhibitor quercetin-3-glucoside (Q3G)) and 75 µM resveratrol (R), 300 µM of the SGLT1 inhibitor Kaempferol-7-glucoside (K7G)) and 75 µM res-veratrol (R), 300 µM of the SGLT1 inhibitor Naringenin-7-glucoside (N7G)) and 75 µM resveratrol (R), 300 µM of the SGLT1 inhibitor Luteolin-7-glucoside(L7G)) and 75 µM piceatannol (P), and 300 µM of the SGLT1 inhibitor Naringenin-7-glucoside(N7G)) and 75 µM piceatannol (P).

EXAMPLE 3

Resistance of Flavonoid Monoglucosides and Dihydrochalcone Monoglucoside to Human Lactase Phloridzin Hydrolase (hLPH) Degradation Preparation of Human Lactase Phloridzin Hydrolase (LPH) Extract Human epithelial colorectal adenocarcinoma (Caco-2) cells were obtained from the American Type Culture Collection (ATCC) and cultured in Dulbeco's modified eagle medium (DMEM) (with GlutaMAX™ I, 4500 mg/L D-glucose, 25 mM HEPES, Invitrogen) +10% foetal calf serum (FCS) (Sigma), MEM non essential amino acids (Fisher Scientific UK Ltd,) and 1.0 mM sodium pyruvate (SIGMA) at confluence for 21 days prior to extraction with a Novagen ProteoExtract™ trans-membrane Protein Extraction kit using "Reagent A" (a mild extraction reagent for recovery of fragile protein complexes) and protease inhibitor cocktail (included in the kit). 200 µl of extract were generated from each T175 $cm^2$ flask. Extracts were stored at −80° C. in 50 ul aliquots. Prior to use extracts were semi-purified, removing low molecular weight interfering components by passing through a small G-25 Sephadex 50-100 µl spin-column (Roche or ThermoFisher Scientific).

hLPH Enzyme Assay

10 µl of semi-purified LPH extract was added to 90 µl of glucoside (1.0 mM final concentration) in 0.1 M maleate (Sigma) buffer, pH 6.0 and incubated for 60 minutes at 37° C. The reaction was terminated by addition of 200 µl 2M Tris (Sigma), pH 8.0. Concurrent blanks were run for each glucoside (1.0 mM) at 37° C. for 60 minutes adding Tris 2 M and then LPH extract only at the end. The 200 µl resultant reaction mix was passed through a small C-18 column (Sep-Pak® Light C18 cartridge 55-105 µm, Waters Ltd.) prepared with (HPLC grade methanol (VWR) and maleate buffer) ×5 times to remove potential interfering hydrophobic LPH extract, substrate (glucoside) and reaction product (aglycone) components. This allowed a full recovery of glucose which was measured using the Amplex® Red Glucose/Glucose Oxidase Assay. Briefly, 100 µl of reaction reagent (0.5° A) 10 mM Ampliflu Red; 1.0% 10 U/ml horseradish peroxidase and 1.0% 100 U/ml glucose oxidase in phosphate buffered saline (PBS), all reagents from SIGMA) was added to 50 µl of sample and incubated at room temperature on an orbital shaker for 20 minutes. Fluorescence was read on a SpectraMax Gemini EM SN plate reader (Molecular Devices) (excitation. 530 nm and emission at 590 nm).

TABLE 2

Glucoside hydrolysis to LPH and resistance relative to Q4G.

| Substrates (1.0 mM) | µM substrate hydrolysed/hr | Resistance to hydrolysis- % Q4G | Supplier |
|---|---|---|---|
| Q3G Quercetin-3-glucoside | 0.178 | 94.26 | SIGMA |
| K3G Kaempferol-3-glucoside | 0.224 | 92.78 | Extrasynthese |

TABLE 2-continued

Glucoside hydrolysis to LPH and resistance relative to Q4G.

| Substrates (1.0 mM) | μM substrate hydrolysed/hr | Resistance to hydrolysis-% Q4G | Supplier |
|---|---|---|---|
| PLZ Phloridzin | 0.507 | 83.64 | SIGMA |
| D8G Daidzein-8-glucoside | 0.552 | 82.19 | SIGMA |
| K7G Kaempferol-7-glucoside | 0.618 | 80.05 | Extrasynthese |
| A8G Apigenin-8-glucoside | 0.685 | 77.90 | SIGMA |
| L7G Luteolin-7-glucoside | 0.814 | 73.72 | Extrasynthese |
| P3G Pelargonidin-3-glucoside | 1.272 | 58.94 | Polyphenols |
| N7G Naringenin-7-glucoside | 1.564 | 49.52 | Extrasynthese |
| Q4G Quercetin-4-glucoside | 3.098 | — | SIGMA |

Glucosides (1.0 mM) were mixed with 10% LPH extract (Caco2 cell-line) for 1 hour at 37° C. The extent of LPH hydrolysis was assessed by measuring glucose reaction product using the Amplex ® Red Glucose/Glucose Oxidase Assay. The table lists those glucosides showing greater resistance to LPH hydrolysis than Q4G.

Table 2 demonstrates the variation in the degradation rates of different flavonoid glucosides by hLPH. Whilst Q4G demonstrates the highest degree of degradation by hLPH, Q3G appears to be approximately 95% more resistant to hLPH in this assay than Q4G. Similarly, the other eight glucosides all exhibit increased resistance to hLPH relative to Q4G, ranging from 49.5% for N7G to 92.8% for K3G. Consequently, these glucosides would be less liable to hydrolysis by hLPH in the intestine during a meal and thus potentially prolonging its activity as a SGLT1 inhibitor. Therefore selecting flavonoid glucosides or dihydrochalcone monoglucosides with at least a 20% increased resistance to hLPH than Q4G would be beneficial in prolonging any glucoside-specific activity in vivo.

EXAMPLE 4

Bottled Water

A dry powder comprising 200 mg quercetin-3-glucoside per gram and 125 mg resveratrol per gram and also comprising flavours is added to water at a level of 2 grams of dry powder per litre of water. The formulation is dispensed into 250 mls bottles and sealed. Each bottle is labelled "1-a-day" or words to that effect. Each bottle therefore delivers a daily dose of 100 mgs quercetin-3-glucoside and 62.5 mgs of resveratrol.

EXAMPLE 5

Sachets for Adding to a Meal

A dry powder comprising 100 mg of luteolin-7-glucoside per gram and 60 mg of resveratrol per gram and also comprising flavours is dispensed into sachets at the level of 1 gram per sachet and sealed. Each sachet is labelled "1-a-day" or words to that effect.

The invention claimed is:

1. A human edible composition, in the form of a single serving of one or more unit dosages, comprising 20-2000 mg of resveratrol and 10-2000 mg of flavonoid monoglucoside or dihydrochalcone monoglucoside; wherein:
   the edible composition is a foodstuff selected from the group consisting of a beverage, a supplement, a soup, margarine, a ready-to-eat meal, a dressing, a mayonnaise, mustard, a tomato-based condiment, a sauce, a seasoning, yoghurt and a frozen confection;
   the dihydrochalcone monoglucoside is phloridzin;
   the flavonoid monoglucoside is selected from the group consisting of luteolin-7-glucoside, apigenin-7-glucoside, apigenin-8-C-glucoside, kaempferol-7-O-glucoside, kaempferol-3-O-glucoside, quercetin-3-glucoside, quercetin-4-glucoside, naringenin-7-O-glucoside, eriodictyol-7-O-glucoside, daidzein-8-C-glucoside, daidzein-7-glucoside, cyanidin-3-glucoside, malvidin-3-O-glucoside, delphinidin-3-glucoside, pelargonidin-3-glucoside and mixtures thereof; and
   the molar ratio of resveratrol to flavonoid monoglucoside or dihydrochalcone monoglucoside is in the range of 1:1 to 1:20.

2. A method of reducing post-prandial blood glucose peak amplitude or glycemic response in a diabetic or non-diabetic person comprising the steps of:
   (a) oral administration of the composition of claim 1 to the diabetic or non-diabetic person; and
   (b) oral administration of a saccharide to the diabetic or non-diabetic person;
   wherein step (a) is simultaneous with, precedes by 0 to 90 minutes, or follows by 0 to 30 minutes step (b), and wherein the saccharide comprises or is glucose.

3. A method for treating a person in need thereof for type 2 diabetes, the method comprising the steps of:
   (a) oral administration of the composition of claim 1 to the person in need thereof; and
   (b) oral administration of a saccharide to the person in need thereof; wherein step (a) is simultaneous with, precedes by 0 to 90 minutes, or follows by 0 to 30 minutes step (b), and wherein the saccharide comprises or is glucose.

4. The method according to claim 2 wherein the saccharide is selected from the group consisting of polysaccharide, oligosaccharide, disaccharide, monosaccharide and mixtures thereof.

5. The composition according to claim 1 comprising 30-1000 mg of resveratrol.

6. The composition according to claim 1 comprising 40-500 mg of resveratrol.

7. The composition according to claim 1 comprising 20-1000 mg of flavonoid monoglucoside or dihydrochalcone monoglucoside.

8. The composition according to claim 1 comprising 40-500 mg of flavonoid monoglucoside or dihydrochalcone monoglucoside.

9. The method of claim 2 wherein step (a) is simultaneous with, precedes by 0 to 60 minutes, or follows by 0 to 30 minutes step (b).

10. The method of claim 3 wherein step (a) is simultaneous with, precedes by 0 to 60 minutes, or follows by 0 to 30 minutes step (b).

11. A human edible composition, in the form of a single serving of one or more unit dosages, wherein the edible composition comprises 20-2000 mg of resveratrol and 10-2000 mg of dihydrochalcone monoglucoside, wherein the dihydrochalcone monoglucoside is phloridzin, and the molar ratio of resveratrol to phloridzin is in the range of 1:1 to 1:20.

12. The composition of claim 11, wherein the molar ratio of resveratrol to phloridzin is in the range of 1:1 to 1:10.

13. The composition of claim 11, wherein the composition is a foodstuff selected from the group consisting of a beverage, a supplement, a soup, margarine, a ready-to-eat meal, a dressing, a mayonnaise, mustard, a tomato-based condiment, a sauce, a seasoning, yoghurt and a frozen confection.

14. The composition of claim 11 comprising 40-500 mg of resveratrol.

15. A human edible composition, in the form of a single serving of one or more unit dosages, wherein the edible composition comprises 20-2000 mg of resveratrol and 10-2000 mg of flavonoid monoglucoside or dihydrochalcone monoglucoside,
wherein:
the edible composition is a foodstuff selected from the group consisting of a beverage, a supplement, a soup, margarine, a ready-to-eat meal, a dressing, a mayonnaise, mustard, a tomato-based condiment, a sauce, a seasoning, yoghurt and a frozen confection;
the dihydrochalcone monoglucoside is phloridzin;
the flavonoid monoglucoside is selected from the group consisting of luteolin-7-glucoside, apigenin-8-C-glucoside, kaempferol-7-O-glucoside, kaempferol-3-O-glucoside, quercetin-3-glucoside, naringenin-7-O-glucoside, and mixtures thereof;
the molar ratio of resveratrol to flavonoid monoglucoside or dihydrochalcone monoglucoside is in the range of 1:1 to 1:10.

16. The composition of claim 15, wherein the foodstuff is a beverage.

17. The composition of claim 15, wherein the foodstuff is a supplement selected from the group consisting of capsules, cachets, lozenges, pills, tablets, and caplets.

18. The composition of claim 15 comprising 40-500 mg of resveratrol.

19. The composition according to claim 1, wherein the molar ratio of resveratrol to flavonoid monoglucoside or dihydrochalcone monoglucoside is in the range of 1:1 to 1:10.

* * * * *